United States Patent
Schock et al.

(10) Patent No.: US 7,229,403 B2
(45) Date of Patent: *Jun. 12, 2007

(54) INTRA-AORTIC BALLOON CATHETER HAVING A DUAL SENSOR PRESSURE SENSING SYSTEM

(75) Inventors: Robert B. Schock, Sparta, NJ (US); Jonathan Williams, Montville, NJ (US); Daniel A. Walters, Rockaway Township, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/435,925

(22) Filed: May 17, 2006

(65) Prior Publication Data
US 2006/0287569 A1 Dec. 21, 2006

Related U.S. Application Data

(63) Continuation of application No. 10/963,273, filed on Oct. 12, 2004, now Pat. No. 7,112,170, which is a continuation of application No. 10/308,638, filed on Dec. 3, 2002, now Pat. No. 6,935,999, which is a continuation of application No. 09/735,076, filed on Dec. 12, 2000, now Pat. No. 6,616,597.

(51) Int. Cl.
*A61M 1/10* (2006.01)
*A61B 5/00* (2006.01)

(52) U.S. Cl. .................. 600/18; 600/486
(58) Field of Classification Search .................. 600/18, 600/465–488, 504, 505; 604/100.01, 101.07, 604/103, 914, 100.07; 128/900
See application file for complete search history.

(56) References Cited

U.S. PATENT DOCUMENTS

| 3,585,983 A | 6/1971 | Kantrowitz et al. |
| 4,175,264 A | 11/1979 | Schiff |
| 4,201,222 A | 5/1980 | Haase |
| 4,733,652 A | 3/1988 | Kantrowitz et al. |

(Continued)

FOREIGN PATENT DOCUMENTS

EP 0 234 046 A 9/1987

(Continued)

OTHER PUBLICATIONS

Operational Instructions for the Corart IABP BP21 from Aisin, Dec. 12, 2002 with partial translation.

(Continued)

*Primary Examiner*—Willis R. Wolfe, Jr.
(74) *Attorney, Agent, or Firm*—Lerner, David, Littenberg, Krumholz & Mentlik, LLP

(57) ABSTRACT

A balloon catheter has a balloon membrane, a tip connected to the distal end of the balloon membrane and an outer tube connected to the proximal end of the balloon membrane for supplying a medium for inflating and deflating the balloon membrane. A pressure sensor, such as a fiber optic sensor, may be mounted in a pocket in the tip. The pocket may be filled with a flexible substance which both communicates pressure to and protects the pressure sensor. A membrane may overlie the pocket to prevent leakage of the flexible substance therefrom.

12 Claims, 7 Drawing Sheets

U.S. PATENT DOCUMENTS

| | | |
|---|---|---|
| 4,966,148 A | 10/1990 | Millar |
| 5,158,529 A | 10/1992 | Kanai |
| 5,202,939 A | 4/1993 | Belleville et al. |
| 5,300,017 A | 4/1994 | Isoyama et al. |
| 5,301,001 A | 4/1994 | Murphy et al. |
| 5,392,117 A | 2/1995 | Belleville et al. |
| 5,427,114 A | 6/1995 | Colliver et al. |
| 5,431,628 A | 7/1995 | Millar |
| 5,505,699 A | 4/1996 | Forman et al. |
| 5,701,905 A | 12/1997 | Esch |
| 5,716,318 A | 2/1998 | Manning |
| 5,716,373 A | 2/1998 | Wolvek et al. |
| 5,779,688 A | 7/1998 | Imran et al. |
| 5,814,016 A | 9/1998 | Valley et al. |
| 5,865,801 A | 2/1999 | Houser |
| 5,902,248 A | 5/1999 | Millar et al. |
| 5,916,153 A | 6/1999 | Rhea, Jr. |
| 6,019,728 A | 2/2000 | Iwata et al. |
| 6,019,729 A | 2/2000 | Itoigawa et al. |
| 6,024,693 A | 2/2000 | Schock et al. |
| 6,231,498 B1 | 5/2001 | Pfeiffer et al. |
| 6,238,382 B1 * | 5/2001 | Schock et al. ............... 604/533 |
| 6,241,706 B1 * | 6/2001 | Leschinsky et al. .......... 600/18 |
| 6,398,738 B1 | 6/2002 | Millar |
| 6,616,597 B2 | 9/2003 | Schock et al. |
| 6,733,459 B1 | 5/2004 | Atsumi |
| 6,935,999 B2 * | 8/2005 | Schock et al. ................. 600/18 |
| 7,112,170 B2 * | 9/2006 | Schock et al. ................. 600/18 |
| 2002/0072679 A1 | 6/2002 | Schock et al. |

FOREIGN PATENT DOCUMENTS

| | | |
|---|---|---|
| EP | 0 307 162 A | 3/1989 |
| EP | 0 577 038 A | 1/1994 |
| EP | 0 609 914 A | 8/1994 |
| EP | 0 611 582 A | 8/1994 |
| EP | 0 674 912 A | 10/1995 |
| EP | 1 016 430 A | 7/2000 |
| JP | 2000-333913 A | 12/2000 |
| WO | WO-97/44084 A | 11/1997 |

OTHER PUBLICATIONS

Product Catalog for the Driving Apparatus for the Corart IABP BP21 from Aisin, Mar. 2004 with partial translation.

Operational Instructions for the Driving Apparatus for the Corart IABP BP21 from Aisin, Nov. 2002 with partial translation.

* cited by examiner

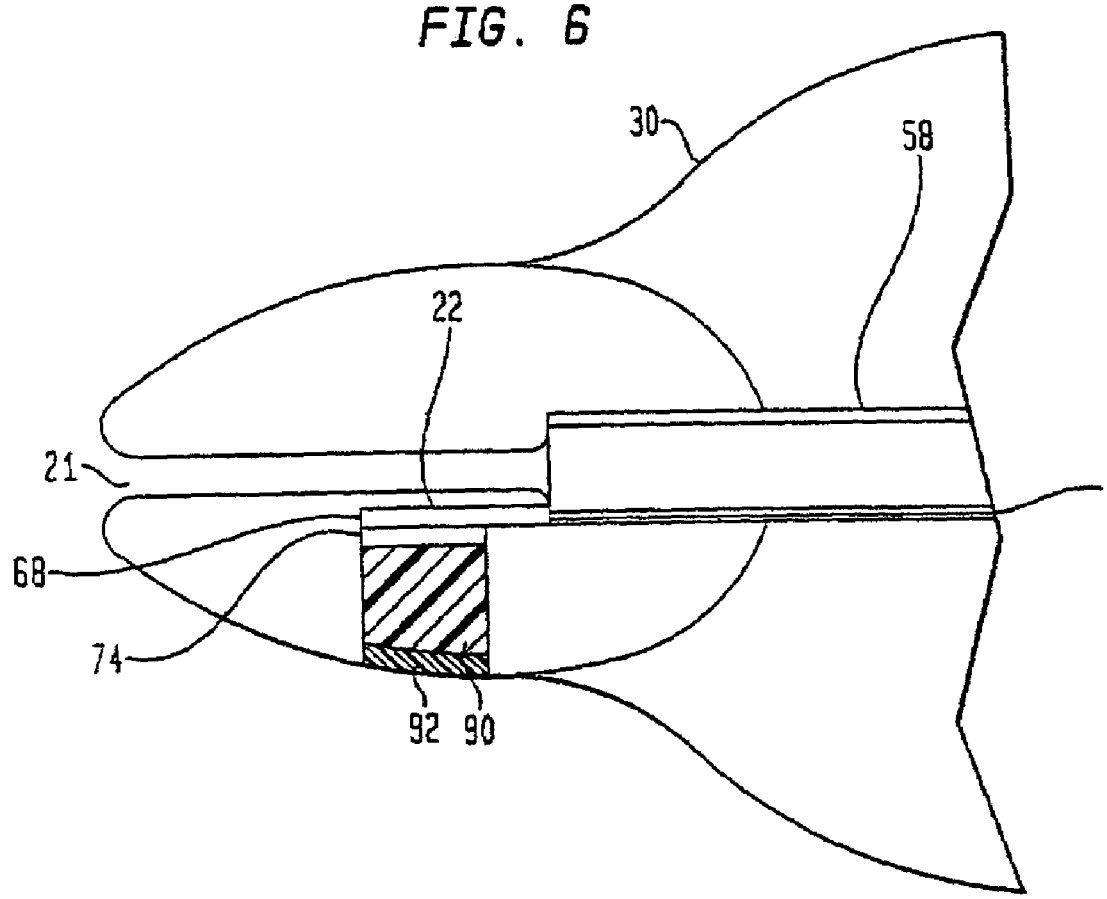

INTRA-AORTIC BALLOON CATHETER HAVING A DUAL SENSOR PRESSURE SENSING SYSTEM

CROSS-REFERENCE TO RELATED APPLICATIONS

The present application is a continuation of U.S. application Ser. No. 10/963,273, filed Oct. 12, 2004, now U.S. Pat. No. 7,112,170 the disclosure of which is hereby incorporated by reference herein, which is a continuation of U.S. application Ser. No. 10/308,638, filed Dec. 3, 2002, now U.S. Pat. No. 6,935,999, which is a continuation of U.S. application Ser. No. 09/735,076, filed Dec. 12, 2000, now U.S. Pat. No. 6,616,597.

BACKGROUND OF THE INVENTION

1. Field of the Invention

The invention relates to a catheter having enhanced pressure sensing capabilities. More particularly, the invention relates to a balloon catheter having a micromanometer connected to the catheter and also a fluid-filled transducer system for adjusting micromanometer pressure measurements.

2. Description of the Prior Art

A key function of many catheters is that of continuously monitoring blood pressure. In many cases, this monitoring must be performed with accurate measurement of high frequency components. For example, reliable detection of the dicrotic notch of the aortic blood pressure waveform typically requires a pressure signal having a bandwidth of 15 Hz or better. Detection of the dicrotic notch is generally used for the inflation/deflation timing of an intra-aortic balloon ("IAB") catheter.

Conventional invasive pressure monitoring is performed with low-cost fluid-filled transducers. A typical disposable monitoring kit, inclusive of all tubing, a continuous flush device, and a pre-calibrated transducer is very affordable. Unfortunately, these systems have several drawbacks. One major drawback is that bubbles or clots in the monitoring lines can reduce the frequency response of the system to a level below 15 Hz, creating an "overdamped" condition. In other cases, the characteristics of the catheter and tubing can result in "ringing", which is associated with an underdamped condition. Furthermore, fluid-filled catheters can suffer from "catheter whip" (motion artifact), which is manifested as one or more high frequency deflections in the pressure signal. These problems can degrade the usefulness of the signal in applications such as intra-aortic balloon pumping (IABP). In particular, it is difficult, if not impossible, to automatically provide optimal timing of IABP using a pressure signal with a frequency response below 15 Hz, or using signals with ringing or whip artifacts that mimic the physiologic dicrotic notch.

Another means for monitoring blood pressure is to use a micromanometer, such as marketed by companies such as Millar, Endosonics, and Radi. See U.S. Pat. Nos. 5,431,628 and 5,902,248, herein incorporated by reference. These devices can have excellent frequency responses, with system bandwidths greater that 200 Hz. They are not subject to the negative effects of bubbles and catheter whip, and retain good performance even in the presence of small blood clots. Unfortunately, they are very expensive, prone to signal drift, and can suffer from electrical interference. A common source of electrical interference in the setting of IABP therapy is the use of electrosurgery. In this situation, it is desirable to maintain a reliable pressure signal with which to trigger the balloon, as the ECG signal which normally triggers IABP operation becomes completely unreliable. Conventional fluid-filled transducer systems are relatively immune from this type of interference.

If the above problems were solved, micromanometers could potentially be used in conjunction with IABP systems and other catheters to measure blood pressure. Attempts have been made to use micromanometers for IABP timing, see U.S. Pat. Nos. 3,585,983 and 4,733,652, herein incorporated by reference. These attempts proved to be unreliable, as the device may be damaged during insertion and is also prone to signal drift. To address the drift issue, U.S. Pat. No. 5,158,529, herein incorporated by reference, discloses a method for rezeroing the micromanometer by using the pressure from a partially filled balloon as it rests in the aorta. However, this method requires momentary interruption of IABP, which may be harmful to the critically ill patient.

While standard IAB catheters incorporating a fluid-filled transducer pressure measurement system or IAB catheters incorporating micromanometers may be suitable for the particular purpose employed, or for general use, they would not be as suitable for the purposes of the present invention as disclosed hereafter.

SUMMARY OF THE INVENTION

Accordingly, there is a need for a reliable and affordable pressure monitoring approach that has high bandwidth pressure sensing, low signal drift, and freedom from electrosurgical interference. There is also a need to incorporate this technology into intra-aortic balloon catheters having small cross sectional profiles.

The invention is an IAB catheter system having enhanced blood pressure sensing capability. The IAB catheter has a micromanometer, or any high fidelity sensor, built into the tip of the IAB or connected to another part of the catheter, and a fluid-filled transducer kit connected to the y-fitting of the IAB. The IABP console, including a processor, continuously monitors and compares signals from both the micromanometer and the fluid-filled transducer. The signal from the micromanometer may be continuously displayed, and either continuously or intermittently adjusted for baseline drift by comparing it to that of the fluid-filled transducer. The adjustment is preferably made by comparing mean blood pressures as indicated by the two sources.

The IABP console could also monitor the micromanometer's signal for the presence of electrosurgical interference, mechanical damage, or any other possible causes of signal error. If significant errors are detected, the system automatically reverts to the use of the signal from the fluid-filled transducer system. The system also allows the user to manually select the use of the fluid-filled transducer, in the event that electrosurgical interference was anticipated.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 6 is a longitudinal cross section of tip 20 and a distal end of inner tube 58 and balloon membrane 30.

DETAILED DESCRIPTION OF THE PREFERRED EMBODIMENTS

Figure 1:
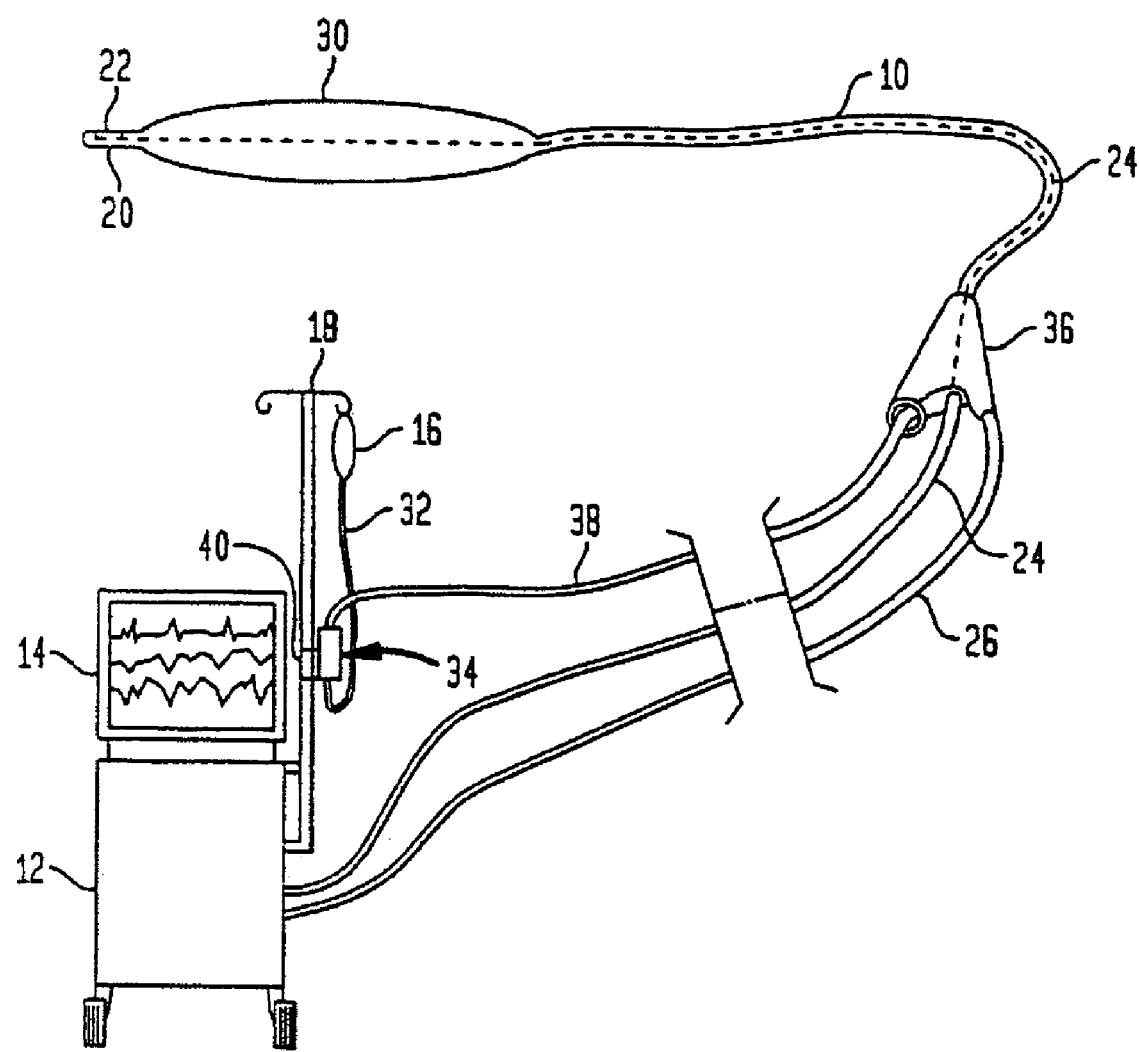
FIG. 1 is a perspective view of the system of the present invention.

FIG. 1 illustrates the system of the present invention comprising an intra-aortic balloon ("IAB") catheter 10, an intra-aortic balloon pump ("IABP") 12, a monitor 14, a drip bag 16, and a drip bag holder 18. FIG. 1 is a perspective view of the system with the IAB catheter 10 in the foreground and the IABP 12 is the background for clarity. The IAB catheter 10 contains a catheter pressure sensor 22 connected to its tip 20 and a Y-fitting 36 on its proximal end. The catheter pressure sensor 22 is connected to the IAB pump 12 via pressure sensing line 24, shown as ghost lines in the IAB catheter 10. Inflate/deflate tube 26, connecting an outer lumen of the IAB catheter 28 (see FIGS. 3–4) and the IABP 12, is used for inflation and deflation of a balloon membrane 30 connected between the tip 20 and a distal end of the IAB catheter 10. Drip tube 32 connects the pressurized drip bag 16 to a flush device 34. Saline tube 38 connects the flush device 34 with an inner lumen 60 of the IAB catheter (see FIGS. 3–4). Clamp 40 connects the flush device 34 to the drip bag holder 18.

Figure 2:
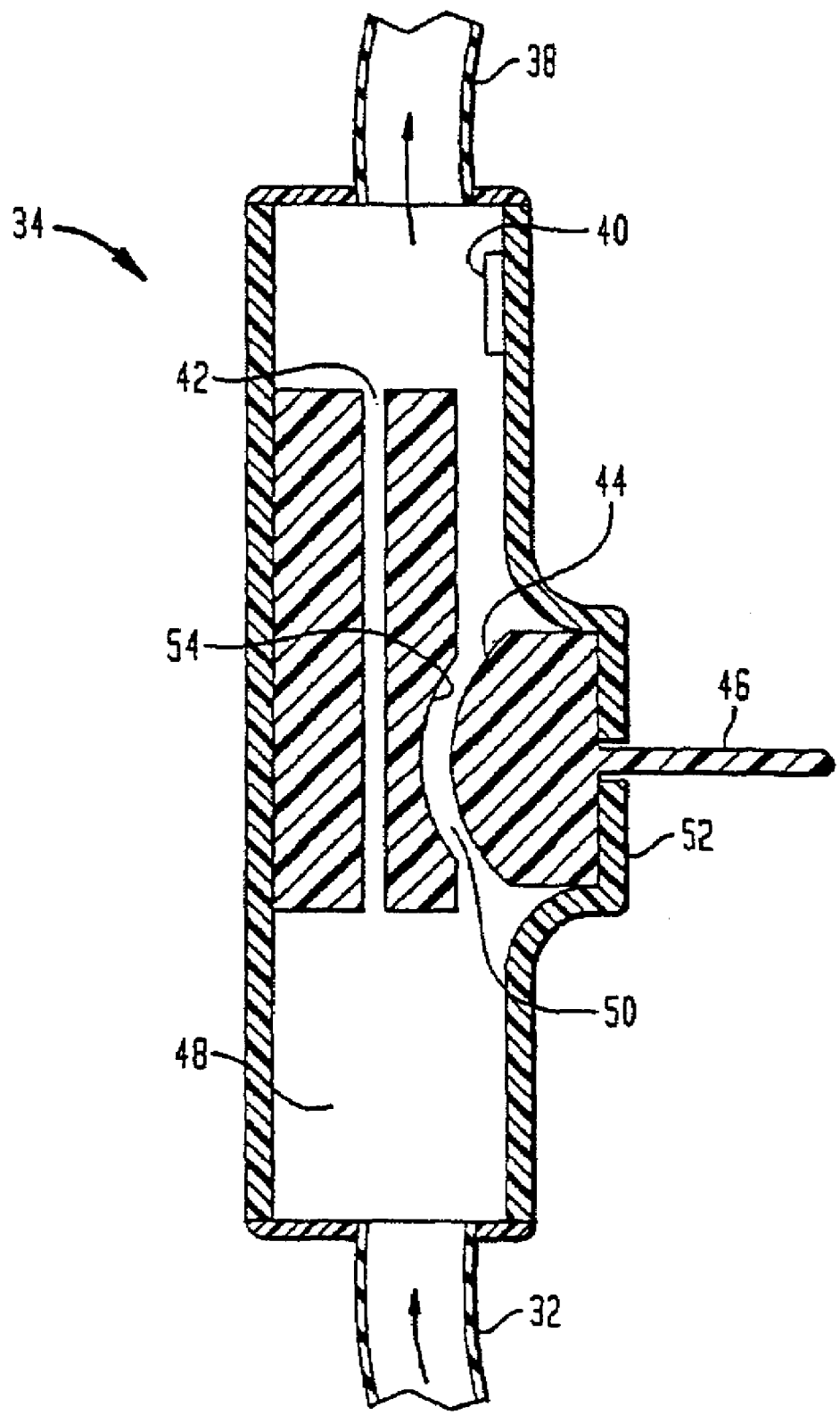
FIG. 2 is a detailed longitudinal cross sectional view of flush device 34 in FIG. 1.

The details of flush device 34 can be seen in FIG. 2. The flush device 34 comprises a flush device wall 52, a microbore passage 42, a fast flush seal 44 having a handle 46, flush device lumen 48, and a fast flush variable lumen 50. Pressure sensor 43 is located in flush device 34 and communicates with IABP 12 via an independent line (not shown), which may exit through a hole (not shown) in flush device wall 52, or in any other means known in the art for electrical devices to communicate. Saline, or another appropriate working fluid or gas, flows through the flush device lumen 48 through the microbore passage 42 at a very slow rate, approximately 3 cc/hour. The pressure on the side of the flush device 34 connected to drip bag 16 equals the pressure in the drip bag 16, generally 300 mmHg. The pressure on the opposite side of the flush device 34 adjacent the pressure sensor 40 equals the blood pressure of the patient being treated with the IAB catheter 10. The fast flush seal 44 is shown in an open state, however, during therapy fast flush seal 44 is forced against seat 54 by the flush device wall 52, and therefore, does not allow saline through fast flush variable lumen 50. In order to fast flush saline tube 38 and bypass microbore passage 42, handle 46 can be pulled away from the flush device 34 such that fast flush seal 44 is lifted off seat 54. During normal operation, however, saline drip is forced through microbore passage 42. Note that the flush device 34 may be replaced with any other known flush device in the art having similar function.

The IABP 12 has incorporated therein a processor that controls the inflation/deflation timing of the balloon membrane 30. Alternatively, the IABP 12 can be connected to a computer or any other type of control mechanism known in the art. The IAB catheter 10 is typically inserted into the femoral artery and moved up the descending thoracic aorta until the distal tip 20 is positioned just below or distal to the left subclavian artery. The proximal end of the catheter remains outside of the patient's body. The patient's central aortic pressure is used to time the inflation and deflation of balloon membrane 30 and the patient's ECG may be used to trigger balloon membrane 30 inflation in synchronous counterpulsation to the patient's heartbeat.

In the preferred embodiment, IABP 12 continuously monitors and compares signals from both saline pressure sensor 40 and catheter pressure sensor 22. The signal derived from catheter pressure sensor 22 may be continuously displayed on monitor 14 and either continuously or intermittently adjusted for baseline drift or other errors by comparing it to that of saline pressure sensor 40. The adjusted signal is displayed on monitor 14 and is used to time the inflation and deflation of the balloon membrane. The balloon membrane is inflated coincident with closure of the aortic valve and is contracted or deflated prior to cardiac ejection.

It is preferred that the adjustment be made by comparing mean blood pressures as indicated by the two sources. In operation pressure would be measured over a predetermined period of time via both the catheter pressure sensor 22 and the saline pressure sensor 40. An indicated mean pressure, based on the catheter pressure sensor 22 measurements, and a true mean pressure, based on the saline pressure sensor 40 measurements, are calculated. If the indicated mean pressure differs from the true mean pressure by less than a predetermined amount, the catheter pressure sensor 22 measurements are displayed without correction; otherwise the catheter pressure sensor measurements are corrected prior to display such that the indicated and true mean pressures are equal. Alternatively, the pressures can be compared on a continuous point-by-point basis and an adjustment made if and when a predetermined pressure differential is reached.

IABP 12 may be programmed to provide options as to which sensor is relied on in any given situation and as how to compare the signals from both sensors and use the information contained in these signals to most accurately measure blood pressure. Note also, that in an alternative embodiment of the invention, a pressure cuff or other external or internal independent device known in the art may replace or act as a backup to the saline pressure sensor 40. The reading from the independent external or internal blood pressure measurement device may be used to correct the drift in the catheter pressure sensor 22 reading in the same manner as used with the saline pressure sensor 40 reading. Use of such an independent external or internal measurement device may be necessary to adjust for drift in tip sensors in intra-aortic catheters without an inner tube and associated saline pressure sensor.

The adjustment to the catheter pressure sensor 22 readings, as described above, involves comparing mean blood pressures. Other methods of adjustment may include comparisons of diastolic pressures, systolic pressures, pressures at the end of balloon inflation, and balloon-augmented pressures. The IABP 12 may also monitor the signal from catheter pressure sensor 22 for the presence of electrosurgical interference, mechanical damage, or any other possible cause of signal error. If significant error is detected, the IABP 12 would automatically revert to use of the signal from saline pressure sensor 40. Similarly, the IABP 12 may monitor the signal from the saline pressure sensor 40 for errors and compensate for these errors by using the signal from the catheter pressure sensor 22. The IABP 12 may optionally allow a user to manually select the use of the saline pressure sensor 40 or the catheter pressure sensor 22. Use of the saline pressure sensor 40 may be desirable in the event that electrosurgical interference was anticipated.

In an alternate embodiment of the invention, rather than adjusting catheter pressure sensor 22 signal for drift, saline pressure sensor 40 signal may be used solely for numerical display purposes and catheter pressure sensor 22 signal used solely for timing the inflation and deflation of balloon membrane 30.

Catheter pressure sensor 22 may include any type of sensor capable of fitting on the catheter and of measuring blood pressure and producing a signal with a frequency response above approximately 15 Hz. Such sensors include but are not limited to micromanometers such as those produced by companies such as Millar, Endosonics, and Radi. These sensors typically include a small transducer exposed to arterial pressure on one side and often a reference pressure on the opposite side. Blood pressure deforms the transducer resulting in a change in resistance which is translated into a pressure reading. Alternatively, a fiber optic sensor may be used in which case pressure sensing line 24 would comprise a fiber optic line. Co-pending application, entitled Intra-Aortic Balloon Catheter Having a Fiberoptic Sensor, filed on Dec. 11, 2000, herein incorporated by reference in its entirety, discloses specific embodiments of an intra-aortic balloon catheter having an incorporated fiberoptic sensor.

Figure 3:
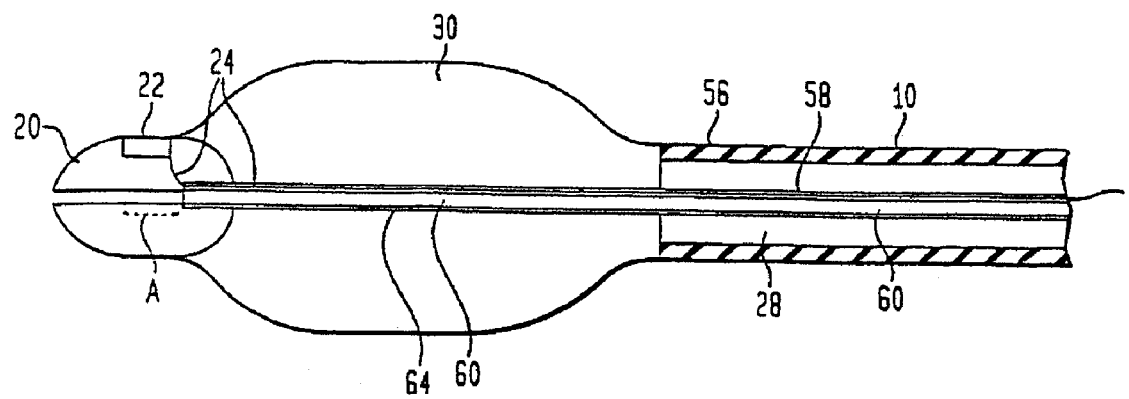
FIG. 3 is longitudinal cross sectional view of a distal portion of IAB catheter 10 in FIG. 1.

The present invention, namely the dual use of both a fluid column pressure sensor and a secondary sensor to measure arterial pressure, is not limited for use with any specific type of catheter. Furthermore, use of different types of intra-aortic balloon catheters is anticipated. FIG. 3 illustrates a longitudinal cross section of a distal portion of a typical dual lumen intra-aortic balloon ("IAB") catheter 10 comprising an outer tube 56, an inner tube 58, a tip 20, and a balloon membrane 30 connected on one end to the outer tube 56 and on the opposite end to the tip 20. Tip 20 defines a tip lumen 21. The inner tube 58 is disposed within the outer tube 56 and is connected to the tip 20 at its distal end. The inner tube 58 defines an inner lumen 60 and the outer tube 56 defines an outer lumen 28. Inner lumen 60 communicates with saline tube 38 and is filled with saline or another suitable fluid for pressure sensing (see FIG. 1). Outer lumen 28 is used for shuttling helium or another appropriate working gas or fluid for inflation and deflation of the balloon membrane 30. The outer tube 56 may be coil or braid reinforced and made from polyurethane or polyimide. Inner tube 58 may be made from polyimide or an alloy with shape memory and superelastic properties commonly referred to as Ni—Ti, NITINOL™, and other industry names. Inner tube 58 may be connected to an inner surface of the outer tube 56 at one or more points or along the entire length of outer tube 56 to enhance pushability, stability, pumping speed, and pressure fidelity. Catheter pressure sensor 22 is embedded in or attached to tip 20.

Pressure sensing line 24 connects catheter pressure sensor 22 to IABP 12 and is sandwiched between the outer surface of inner tube 58 and a secondary layer 64. Alternatively, the pressure sensing line 24 is embedded in inner tube 58 or attached to the outer surface of inner tube 58 (see discussion of FIGS. 3A–3C below). Pressure sensing line 24 will vary dependent on the type of sensor used. If an electrical micromanometer of half-bridge design is used pressure sensing line 24 may consist of three fine wires 62 (see FIGS. 3A–3C), each approximately 0.001 inches in diameter. Note that the catheter pressure sensor 22 may be positioned in alternate locations along IAB catheter 10 as well as on a distal tip of an independent catheter that can be disposed within the inner lumen 58. Dotted box, labeled A, designates another area where the catheter pressure sensor 22 may be located. In this location catheter pressure sensor 22 is exposed to arterial pressure via tip lumen 21 and is less likely to be damaged upon insertion and placement of IAB catheter 10.

Figure 3A:
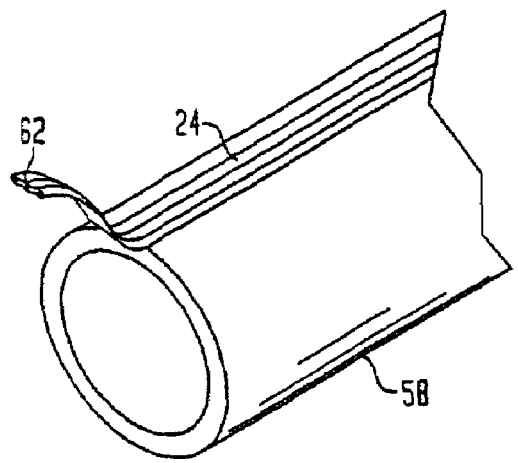
FIG. 3A is a perspective view of distal end of inner tube 58, shown independent of catheter 10, with pressure sensing line 24 connected to an outer surface of inner tube 58.
Figure 3B:
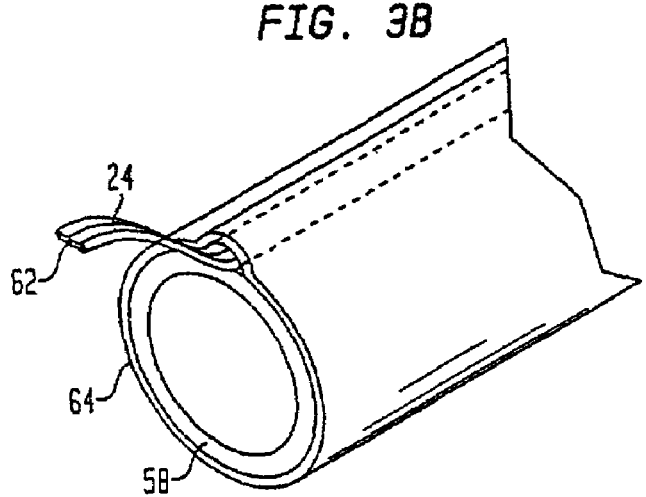
FIG. 3B a perspective view of a distal end of inner tube 58, shown independent of catheter 10, with pressure sensing line sandwiched between an outer surface of inner tube 58 and an outer layer.
Figure 3C:
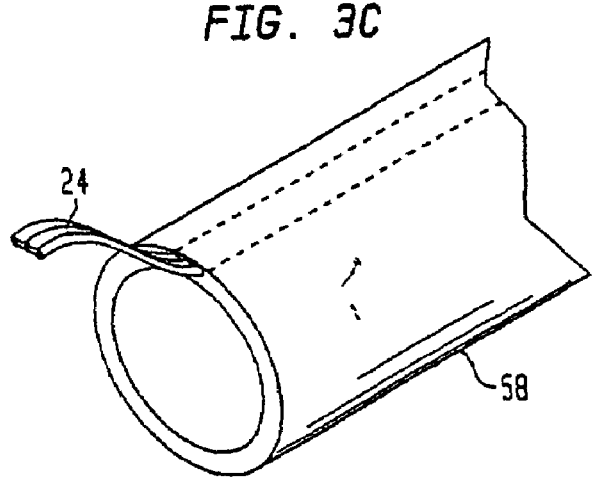
FIG. 3C is a perspective view of a distal end of inner tube 58, shown independent of catheter 10, with pressure sensing line 24 embedded in the wall of inner tube 58.

FIGS. 3A–3C illustrate transverse cross sections of inner tube 58 with pressure sensing line 24 connected to inner tube 58 in various configurations. In FIG. 3A, pressure sensing line 24, comprising three fine wires 62, is connected to an outer surface of inner tube 58. In FIG. 3B, pressure sensing line 24 is disposed between inner tube 58 and a thin walled tube 64, which preferably is heat shrinkable. In FIG. 3C, pressure sensing line 24 is embedded in the wall of inner tube 58. Note that although pressure sensing line 24 is shown running along a longitudinal axis of inner tube 58 it may also be wound helically.

Figure 4:
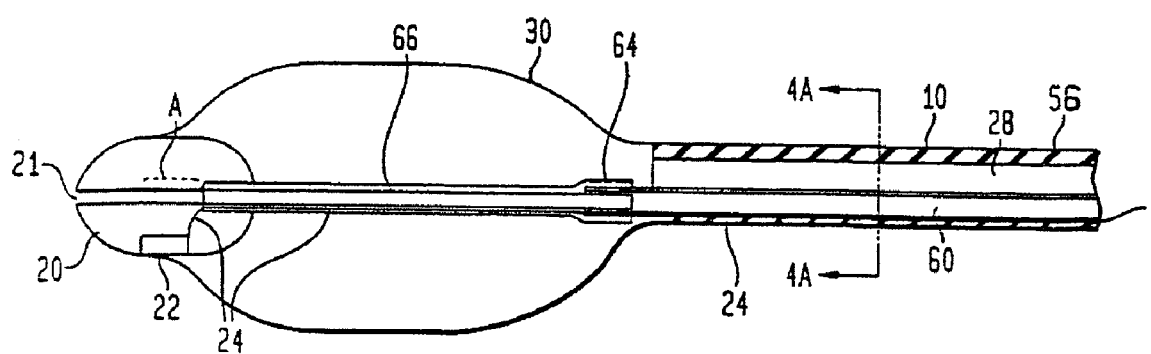
FIG. 4 is a longitudinal cross sectional view of a distal portion of a co-lumen IAB catheter having a pressure sensor embedded in the tip.

FIG. 4 illustrates a distal portion of another embodiment of the IAB catheter 10, comprising a balloon membrane 30, a tip 20, a co-lumen tube 56, an inner lumen extension tube 66, and a catheter pressure sensor 22. Detailed structure of a co-lumen IAB is disclosed in U.S. Pat. No. 6,024,693 and U.S. patent application Ser. No. 09/412,718, filed on Oct. 5, 1999, both herein incorporated by reference. Tip 20 is connected to a distal end of the balloon membrane 30 and to a distal end of the inner lumen extension tube 66. Tip 20 defines a tip lumen 21. A distal end of the co-lumen tube 56 is connected to a proximal end of the balloon membrane 30 and to a proximal end of the inner lumen extension tube 66. The co-lumen tube 56 may be coil or braid reinforced and made from polyurethane or polyimide. The preferred material for inner lumen extension tube 66 is an alloy with shape memory and superelastic properties commonly referred to as Ni—Ti, NITINOL™, and other industry names. Inner lumen extension tube 66 may also be made from polyimide. The catheter pressure sensor 22 is attached to tip 20 and pressure sensing line 24 which communicates signals generated by the catheter pressure sensor 22 to the IABP 12 (see FIG. 1).

Figure 4A:
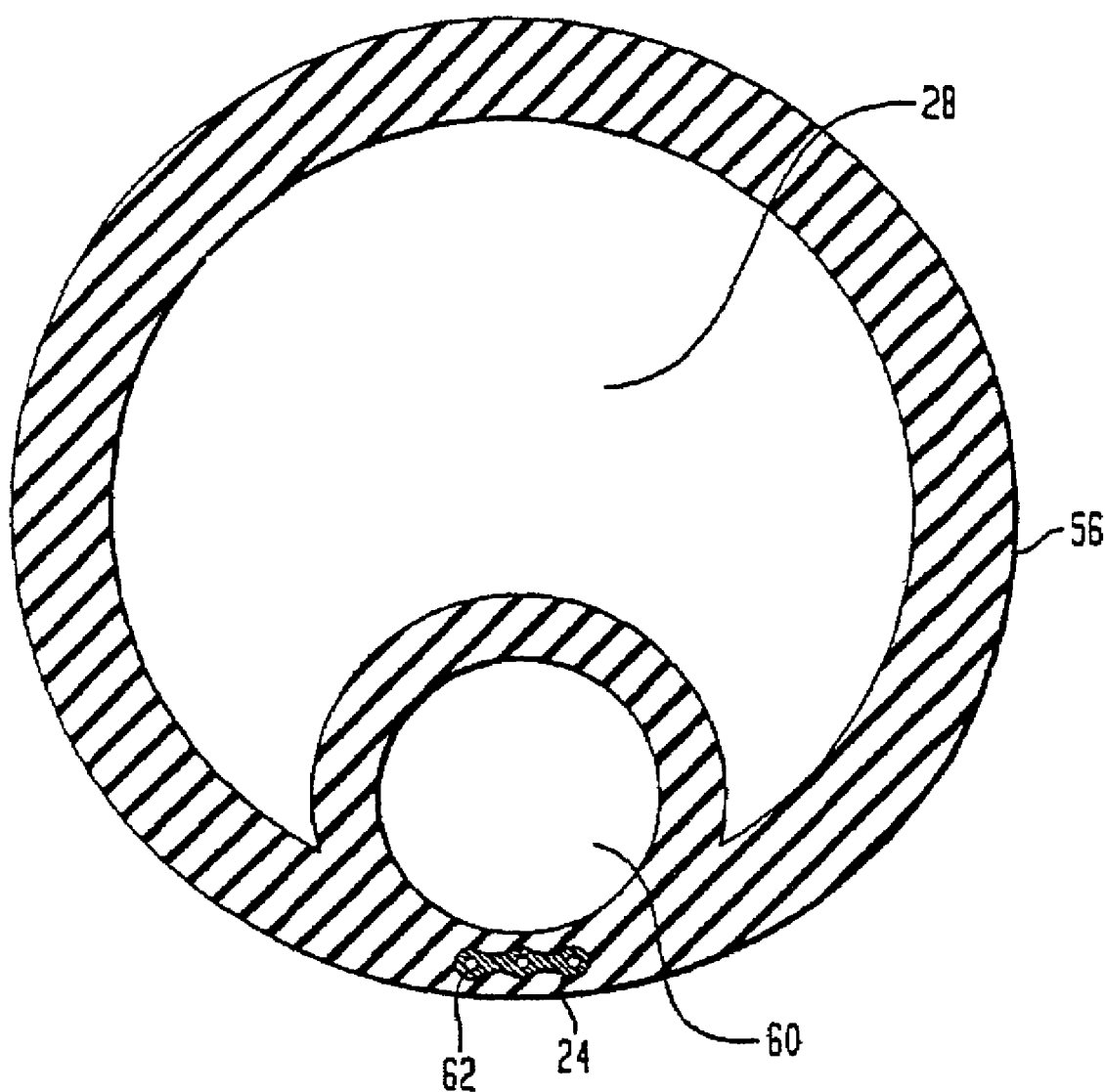
FIG. 4A is a transverse cross section of the co-lumen IAB, taken along lines 4A—4A in FIG. 4.

Pressure sensing line 24, as illustrated in FIG. 4, is sandwiched between inner lumen extension tube 66 and thin walled tube 64; however, pressure sensing line 24 may be connected to the inner lumen extension tube 66 in any of the ways illustrated in FIGS. 3A–3C. It is preferred that pressure sensing line 24 float freely in outer lumen 28, as illustrated in FIG. 4, however, pressure sensing line 24 may be connected to co-lumen tube 56 in any of the ways illustrated in FIGS. 3A–3C. FIG. 4A illustrates a transverse cross section of outer tube 56, taken along line 4A—4A illustrated in FIG. 4, with pressure sensing line 24 embedded in the wall. Note that pressure sensing line 24 may be embedded at a different location in co-lumen tube 56 or connected to a surface of co-lumen tube 56.

Co-lumen tube 56 defines two distinct lumens, inner lumen 63 and outer lumen 28. Inner lumen 60 communicates with saline tube 38 (see FIG. 1). Outer lumen 28 communicates with inflate/deflate tube 26 and is used for shuttling helium or another appropriate fluid or gas for inflation and deflation of balloon membrane 30. Note that the catheter pressure sensor 22 may be positioned in alternate locations along IAB catheter 10 as well as on a distal tip of an independent catheter that can be disposed within the inner lumen 58. Dotted box, labeled A, designates another area where the catheter pressure sensor 22 may be located. In this location catheter pressure sensor 22 is exposed to arterial pressure via tip lumen 21 and is less likely to be damaged upon insertion and placement of IAB catheter 10.

Figure 5A:
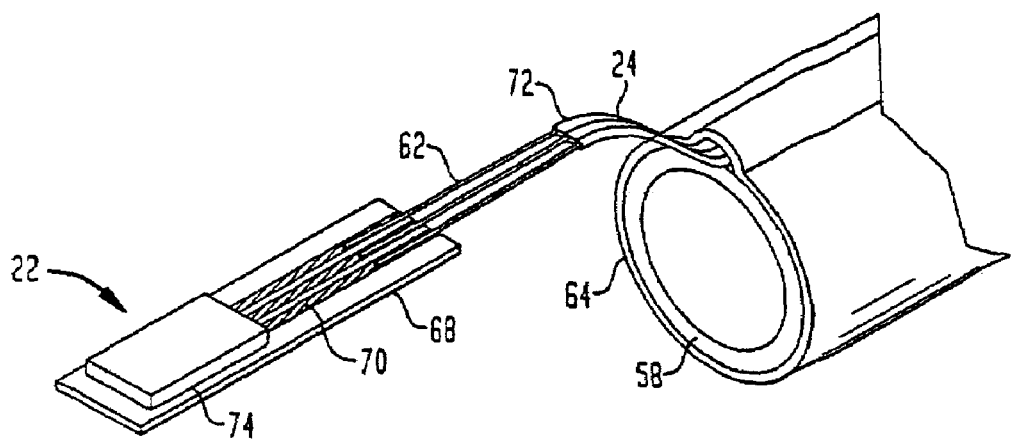
FIG. 5A is a perspective view of a distal end of the inner tube 58 and the catheter pressure sensor 22, illustrating a first connection scheme.
Figure 5B:
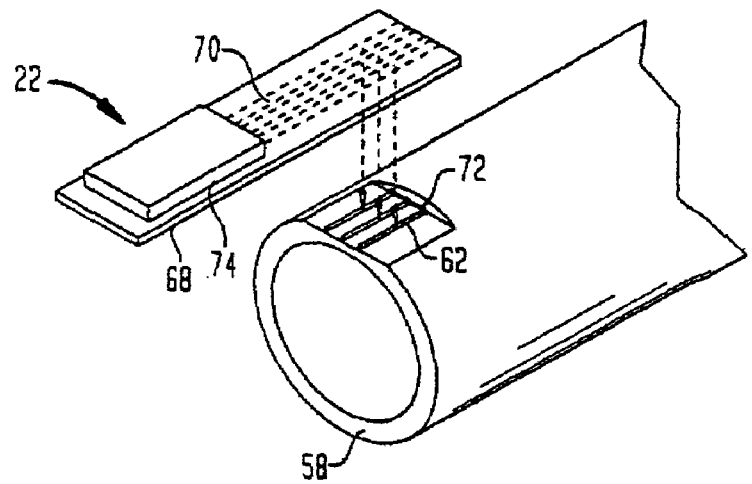
FIG. 5B is a perspective view of a distal end of the inner tube 58 and the catheter pressure sensor 22, illustrating a second connection scheme.
Figure 5C:
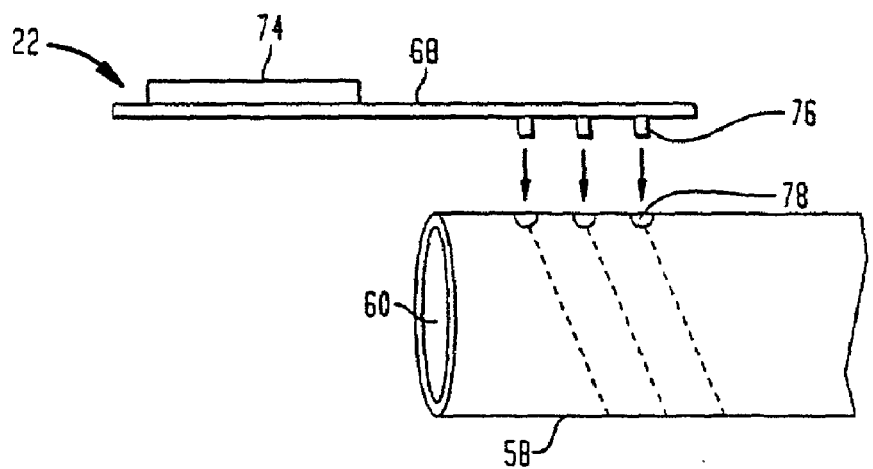
FIG. 5C is a perspective view of a distal end of the inner tube 58 and the catheter pressure sensor 22, illustrating a third connection scheme.

FIGS. 5A–5C illustrate in detail alternate connections between catheter pressure sensor 22 and a distal end of pressure sensing line 24. In FIG. 5A a distal end of pressure sensing line 24, extending beyond a distal end of either inner tube 58 (FIG. 3) or inner lumen extension tube 66 (FIG. 4), is stripped of insulation 72 exposing wires 62. Catheter pressure sensor 22 comprises a transducer 74 connected to a support 68. Exposed wires 62 are positioned over contacts 70 on support 68 and may be soldered to support 68. Note that pressure sensing line 24 is connected to inner tube 58 as shown in FIG. 3B, however, connections shown in FIGS. 3A and 3C may also be used.

FIG. 5B illustrates an alternate connection between catheter pressure sensor 22 and pressure sensing line 24, which is embedded in inner tube 58. This connection may be used when catheter pressure sensor 22 is located in alternate location A (see FIGS. 3 and 4). Catheter pressure sensor 22 is identical to the embodiment in FIG. 5A except contacts 70 are on the underside of the support 68. Wires 62 are exposed by peeling off insulation 72 and a portion of inner tube 58 directly above pressure sensing line 24. Catheter pressure sensor 22 fits directly on top of pressure sensing line 24 such that wires 62 fit over contacts 70. Rather than stripping away an entire section of inner tube 58, as in FIG. 5B, small holes 78 could be made over the ends of each wire 62, as illustrated in FIG. 5C. Solder pads 76 project from an under side of catheter pressure sensor 22. Holes 78 can be aligned perpendicular to the longitudinal axis of the tube or if the wires are wound helically, see dotted lines in FIG. 5C, the holes can be aligned along the longitudinal axis of the inner tube 58. Note that catheter pressure sensor 22 may shifted proximally such that it does not overhang the distal end of inner tube 58. In such case, an additional hole through inner tube 58 may be used to allow transducer 74, which is placed over such hole, to communicate with inner lumen 60.

Alternatively, transducer 74 may face toward an outer surface of catheter tip 20 and sense pressure on the outside of tip 20. This can be accomplished by using a thicker support 68 or by creating a pocket 90 over transducer 74, as illustrated in FIG. 6. FIG. 6 is a longitudinal cross section of tip 20 and a distal end of inner tube 58 and balloon membrane 30. Tip 20 has a pocket 90 directly over transducer 74. Pocket 90 may contain a gel, fluid, gas, elastomer, or any other flexible substance which both communicates pressure and protects transducer 74. Membrane 92 prevents leakage of gel or other substance from pocket 90. As an alternative to the use of membrane 92, balloon membrane 30 can be extended to cover pocket 90. This catheter pressure sensor 22 arrangement can be used for both the dual lumen (FIG. 3) and co-lumen catheters (FIG. 4).

Note that for both the typical dual lumen and co-lumen catheter arrangements the portion of the inner tube 58 disposed within the balloon membrane 30 may be made from a different material from the rest of the inner tube 58. This can be accomplished by connecting two separate pieces of tubing as disclosed in U.S. Pat. No. 6,024,693, assigned to Datascope Investment Corp., herein incorporated by reference in its entirety.

As many apparently widely different embodiments of the present invention can be made without departing from the spirit and scope thereof, it is to be understood that the invention is not limited to the specific embodiments thereof except as defined in the appended claims.

The invention claimed is:

1. An intra-aortic balloon pump system, comprising:
an intra-aortic balloon pump;
a balloon catheter connected to the intra-aortic balloon pump, the balloon catheter including a balloon membrane, an outer tube, a tip, and a catheter pressure sensor connected to the balloon catheter, a distal end of the balloon membrane being connected to the tip, and a proximal end of the balloon membrane being connected to the outer tube; and
an independent blood pressure measurement device connected to the intra-aortic balloon pump.

2. The intra-aortic balloon pump system as claimed in claim 1, wherein the catheter pressure sensor includes a fiber optic sensor.

3. The intra-aortic balloon pump system as claimed in claim 1; wherein the catheter pressure sensor includes a transducer.

4. The intra-aortic balloon pump system as claimed in claim 1, wherein the independent blood pressure measurement device includes a blood pressure cuff.

5. An intra-aortic balloon pump system, comprising:
an intra-aortic balloon pump;
a balloon catheter connected to the intra-aortic balloon pump, the balloon catheter including a balloon membrane, a conduit connected to a proximal end of the balloon membrane, a tip connected to a distal end of the balloon membrane, the tip having a pocket therein, a pressure sensor mounted to the tip within the pocket, and a protective material overlying the pressure sensor, the protective material being selected from the group consisting of a gel, a fluid and a gas.

6. The intra-aortic balloon pump system as claimed in claim 5, wherein the pocket is exposed to an exterior of the tip.

7. The intra-aortic balloon pump system as claimed in claim 5, wherein the pressure sensor includes a fiber optic sensor.

8. The intra-aortic balloon pump system as claimed in claim 5, further comprising a membrane overlying the pocket in the tip.

9. The intra-aortic balloon pump system as claimed in claim 8, wherein the membrane is the balloon membrane.

10. An intra-aortic balloon pump system, comprising:
an intra-aortic balloon pump;
a balloon catheter connected to the intra-aortic balloon pump, the balloon catheter including a balloon membrane, a tip, and an outer tube, a distal end of the balloon membrane being connected to the tip, and a proximal end of the balloon membrane being connected to the outer tube;

a measurement system connected to the intra-aortic balloon pump and adapted to be fluid-filled, the measurement system being connectable to a fluid source and to the outer tube via a fluid source line, and being connectable to a first pressure sensor for measuring pressure in the fluid source line; and a second pressure sensor connected to the balloon catheter, the second pressure sensor including a fiber optic sensor.

11. The intra-aortic balloon pump system as claimed in claim 10, wherein the tip comprises a tip lumin, an outer surface, and a pocket in the outer surface, and wherein the second pressure sensor is mounted to the tip with at least one surface of the second pressure sensor exposed in the pocket.

12. The intra-aortic balloon pump system as claimed in claim 11, wherein the pocket is filled with a protective material.

* * * * *